(12) United States Patent
Wellisz

(10) Patent No.: US 6,923,812 B1
(45) Date of Patent: Aug. 2, 2005

(54) BARBED CLIP FOR BONE ALIGNMENT AND FIXATION

(75) Inventor: Tadeusz Z. Wellisz, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 569 days.

(21) Appl. No.: 09/840,441

(22) Filed: Jul. 30, 2001

(51) Int. Cl.⁷ .............................................. A61B 17/56
(52) U.S. Cl. .......................... 606/72; 606/69; 606/151
(58) Field of Search .............................. 606/71, 69, 72, 606/70, 75, 86, 104, 151, 53, 77; 29/243.56; 248/205.1, 216.4, 217.2, 217.3, 905

(56) References Cited

U.S. PATENT DOCUMENTS

| 3,858,370 | A | * | 1/1975 | Halstead ..................... 312/352 |
| 4,255,910 | A | * | 3/1981 | Wendt ....................... 52/481.2 |
| 4,333,625 | A | * | 6/1982 | Haug ....................... 248/216.1 |
| 5,487,741 | A | * | 1/1996 | Maruyama et al. ........... 606/60 |
| 5,707,373 | A | * | 1/1998 | Sevrain et al. ................ 606/72 |
| 5,800,436 | A | * | 9/1998 | Lerch .......................... 606/72 |
| 5,916,217 | A | * | 6/1999 | Manthrop et al. ............ 606/72 |
| 5,941,878 | A | * | 8/1999 | Medoff ........................ 606/60 |
| 6,168,596 | B1 |  | 1/2001 | Wellisz et al. |
| 6,190,389 | B1 |  | 2/2001 | Wellisz et al. |
| 6,582,435 | B2 | * | 6/2003 | Wellisz et al. ................ 606/72 |
| 6,652,531 | B2 | * | 11/2003 | Wellisz et al. ............... 606/72 |
| 6,679,885 | B2 | * | 1/2004 | Wellisz ........................ 606/72 |
| 6,709,437 | B2 | * | 3/2004 | Wellisz ........................ 606/71 |
| 2002/0156477 | A1 | * | 10/2002 | Knopfle et al. ............... 606/75 |

* cited by examiner

Primary Examiner—Henry Bennett
Assistant Examiner—Kathryn Odland
(74) Attorney, Agent, or Firm—William W. Haefliger

(57) ABSTRACT

A clip to interconnect primary and secondary bone zones having edges and surfaces, comprising in combination a first tab to extend proximate a surface of the secondary bone zone; a second tab associated with the first tab, and located to extend proximate a surface of the primary bone zone, the second tab having at least one barb oriented to engage the primary bone to resist displacement of the second tab in a longitudinal direction toward the secondary bone zone.

16 Claims, 4 Drawing Sheets

Figure 5:
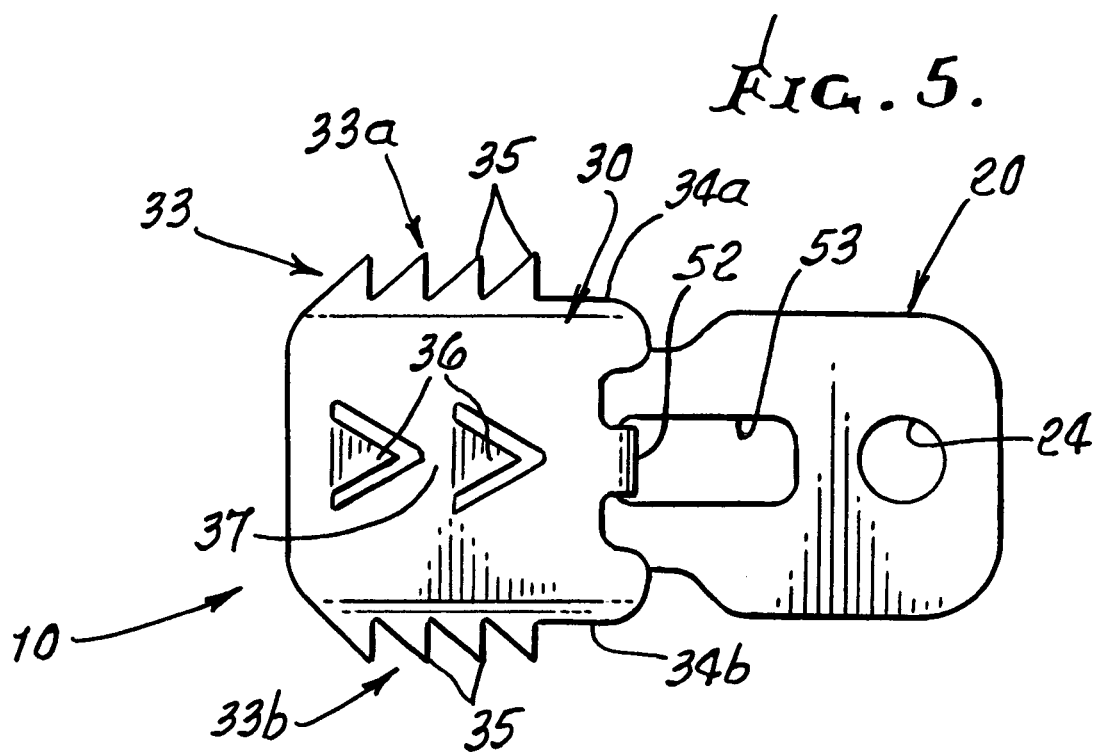

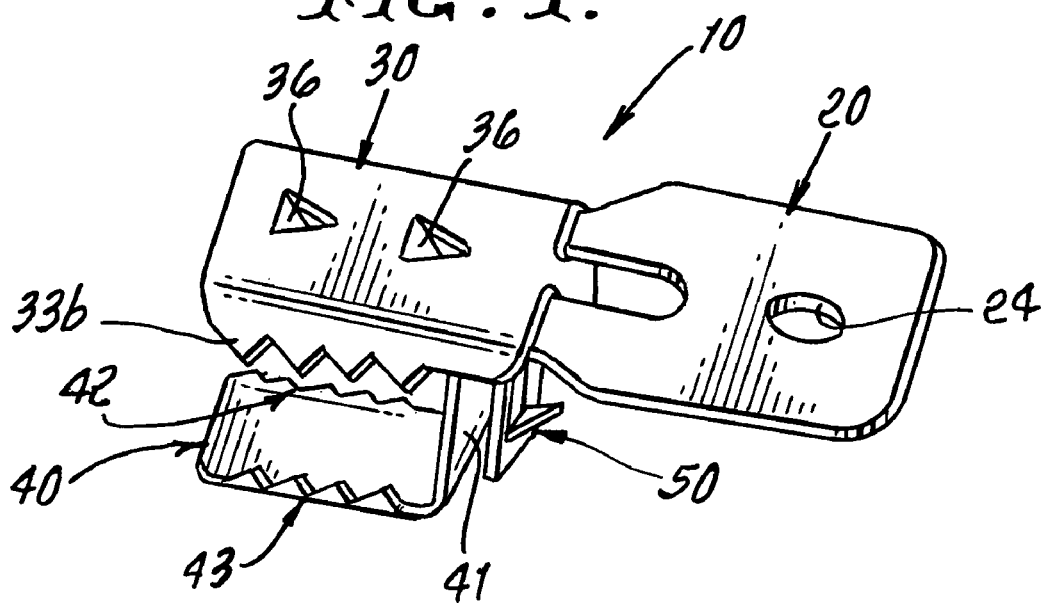
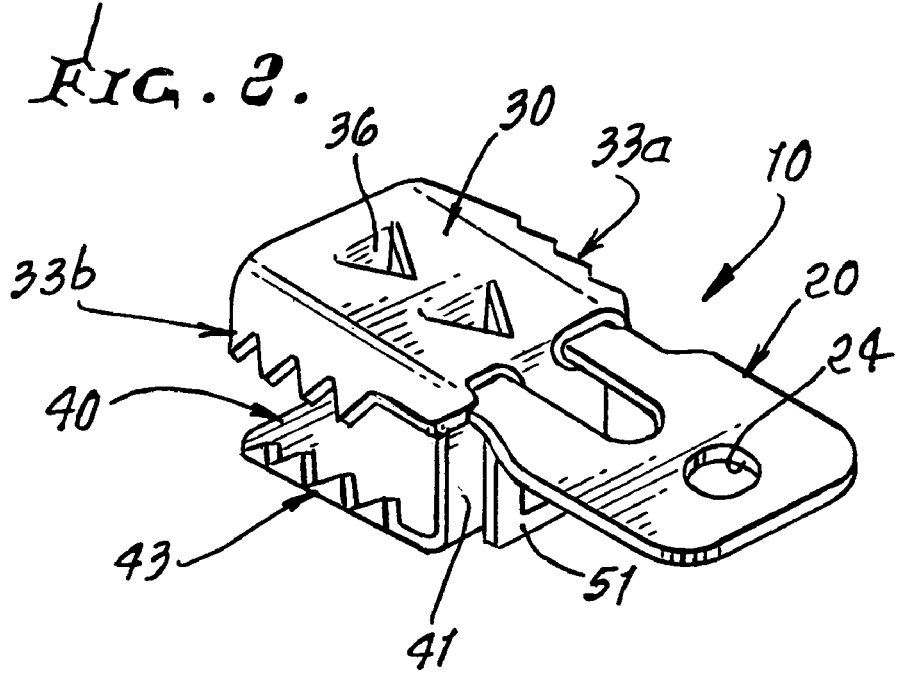

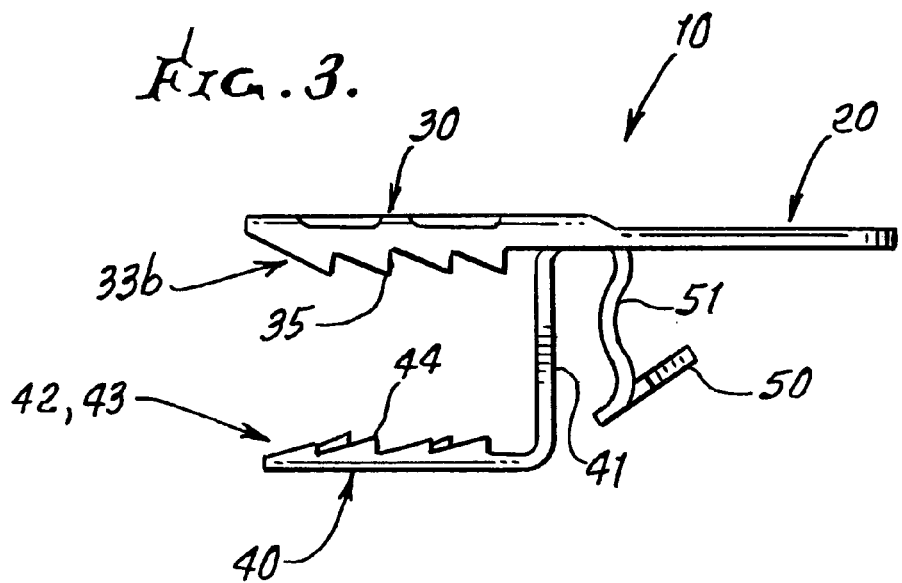
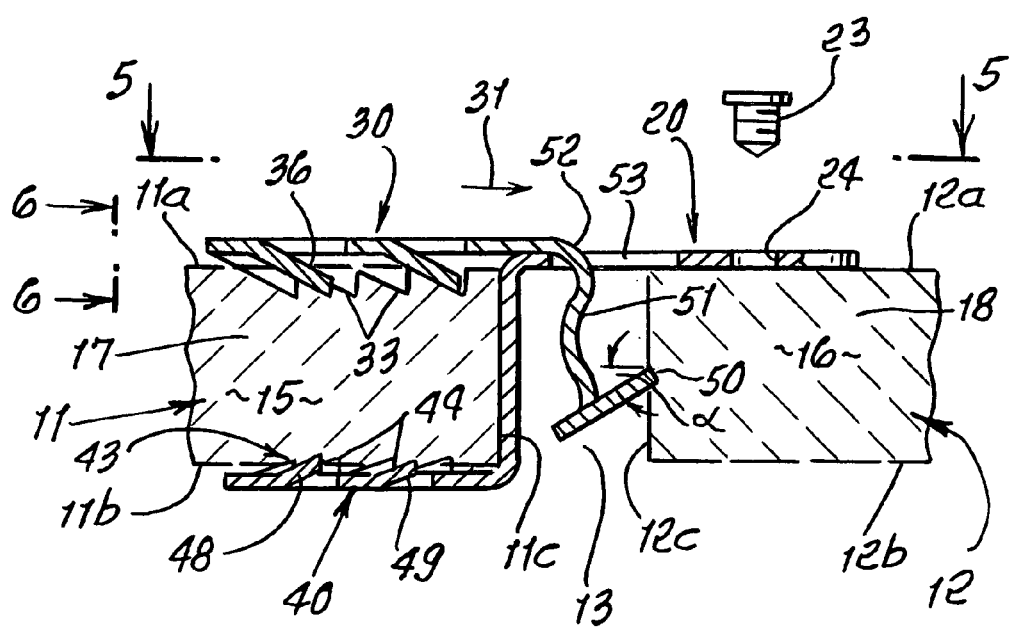

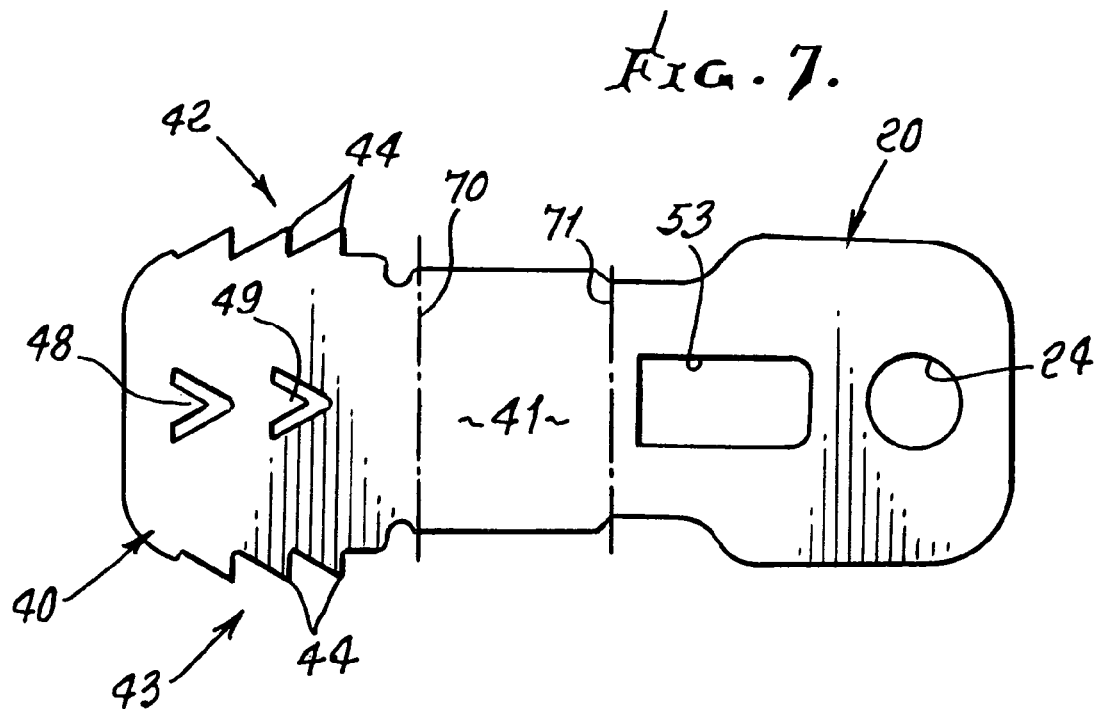
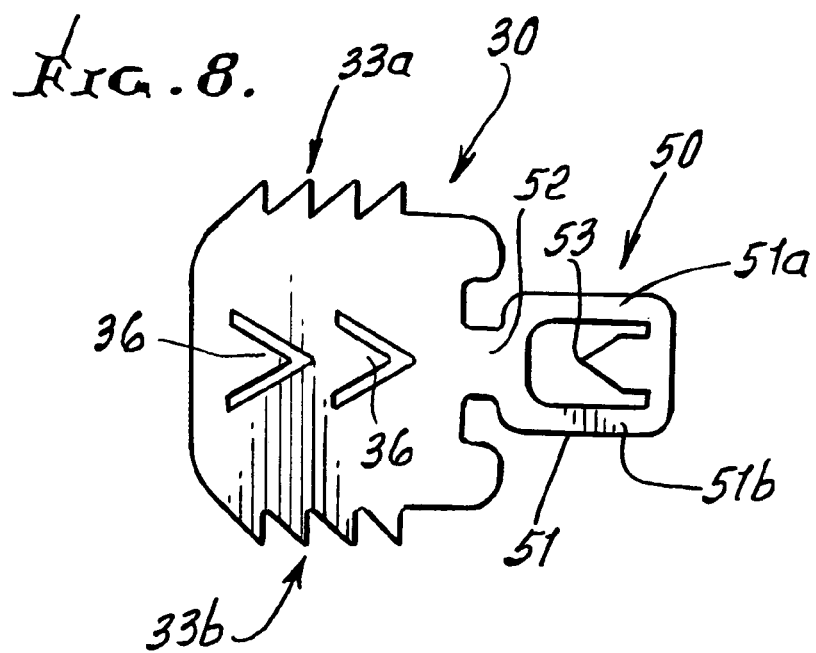

BARBED CLIP FOR BONE ALIGNMENT AND FIXATION

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the diploe which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos. 5,372, 598; 5,413,577; and 5,578,036). A plate made of metal or other substance can be fixated to the outer cortex of the primary bone zone with screws whose penetration of the bone can be limited to the outer cortex. With three or more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems allow for the alignment and fixation of the zones, while preventing the primary bone zone from falling below the level of the secondary bone zone without actually introducing a component of the device below the secondary bone zone. A plate with a spring clip extension has been described (U.S. Pat. No. 5,916,217). Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation (U.S. Pat. No. 5,501,685); however, the bone zones can not be aligned in three dimensions with this technique.

There is a need for an alignment and fixation device that is simple and rapid to use, versatile, and ultimately cost effective.

OBJECTS OF THE INVENTION

The object of the invention is to provide a device and instruments for its use that aligns the one cortex of a primary zone with one cortex of a secondary bone zone without extending to the opposing cortex, and which fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones. The alignment feature can be used independently from the fixation feature. An example of the use of the alignment feature is in the replacement of a cranial bone fragment which will be held in place by the tissue forces of the scalp, which allows for the bone fragment to be elevated away from the cranial cavity in cases where brain swelling occurs. Fixation can also be applied to attach the alignment device to the bone, using elements alone or in combination such as filaments, screws, rivets, pins, clips, cams, friction or adhesives. The alignment aspect of the invention can also be applied to situations where it is desired to offset the alignment of the bone fragment to the adjacent bone such as where the object is to create a more prominent chin by cutting the bone of the chin and advancing the bone fragment.

The fixation feature of the invention is likewise independent from the alignment feature. The fixation feature of the device relies on the principle that the device is fixated to the primary bone zone and the fixation feature grips the secondary bone zone by means of spring loaded tab or hook elements engaging the soft areas of the medullary space, irregularities along the cut surface, or a slot cut into the cut surface of the secondary bone zone.

SUMMARY OF THE INVENTION

The invention provides an improved clip meeting the above need or needs.

As will be seen the preferred clip is configured to interconnect primary and secondary bone zones having edges spaced apart by a gap, the clip comprising
  a) a first tab to extend proximate a surface of the secondary bone zone,
  b) a second tab associated with the first tab, and located to extend proximate a surface of the primary bone zone,
  c) the second tab having at least one barb oriented to engage the primary bone to resist displacement of the second tab in a longitudinal direction toward the secondary bone zone.

As will be seen, the barb may be located at an edge of the second tab; and the barb may have a tip offset from a plane defined by the second tab. In this regard, the second tab preferably has a multiplicity of barbs oriented to engage the primary bone zone to resist displacement of the second tab in the direction toward the secondary bone zone. Such barbs may typically extend in at least one row, in said direction; and they preferably extend in two parallel generally longitudinal rows. An anchor element is typically provided on the first tab for use in anchoring the first tab to the secondary bone zone.

Another object includes provision of a retainer operatively connected with at least one of the first and second tabs and projecting for retention to at least one of the bone zones at a retention level spaced from levels defined by those tabs. That retainer typically comprises a third tab spaced from the first and second tabs. Also, the third tab preferably has a multiplicity of barbs oriented to engage the primary bone zone to resist displacement of the third tab in the direction toward the secondary bone zone.

A yet further object includes provision of a projection associated with at least one of the tabs, and configured to engage the secondary bone zone at the edge thereof, and in spaced relation to the tabs. That projection typically has a sharp terminal to enable penetration of diploe; and it extends at an acute angle relative to a plane defined by said one tab. Further, a spring arm typically connects the projection to the at least one tab, so that the projection extends downwardly into a gap formed by edges of the primary and secondary bone zones.

These and other objects and advantages of the invention, as well as the details of an illustrative embodiment, will be more fully understood from the following specification and drawings, in which:

DRAWING DESCRIPTION

Figure 6:
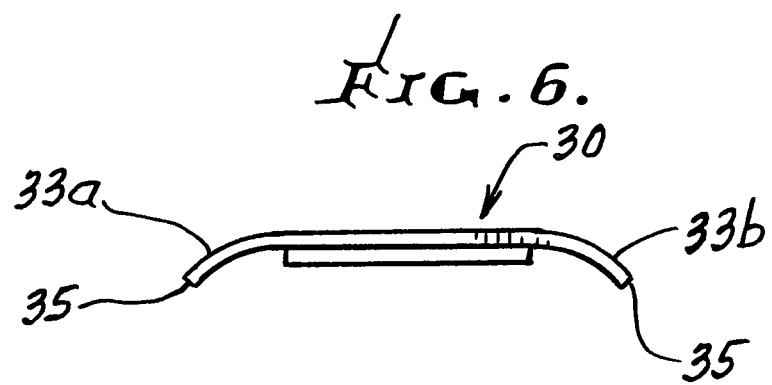

FIGS. 1 and 2 are perspective views of a preferred form of clip embodying features of the invention;
FIG. 3 is a side elevational view of the FIG. 1 clip;
FIG. 4 is another side elevational view of the FIG. 1 clip;
FIG. 5 is a top plan view taken on lines 5—5 of FIG. 4;
FIG. 6 is a first elevational view taken on lines 6—6 of FIG. 4;
FIG. 7 is a top plan view of a blank from which a structural component part of the clip is to be formed; and
FIG. 8 is a top plan view of a blank from which a spring component part of the clip is to be formed.

DETAILED DESCRIPTION

In FIGS. 1–5, the illustrated clip 10 is configured to interconnect primary and secondary bone zones 11 and 12, having opposed and spaced apart edges 11c and 12c. A cut or gap 13 is formed between the opposed edges of the primary and secondary bone zones. Diploe is shown at 15 between the top and bottom surfaces 11a and 11b of zone 11; and at 16 between the top and bottom surfaces 12a and 12b of zone 12. As also seen in FIG. 4, primary bone zone 11 may be defined by bone flap 17; and secondary bone zone 12 may be defined by skull 18 and its zone extents at 12 opposing zone 11. In the adult, cranial bone or skull averages 7 mm in thickness, but varies between 3 and 12 mm.

The clip 10, which is preferably metallic includes the following a) a first tab 20 to extend proximate and on a surface 12a of the secondary bone zone 12, b) a second tab 30 associated with the first tab 20, and located to extend proximate and on a surface 11a of the primary bone zone 11, c) the second tab 30 having at least one barb oriented to engage the primary bone zone 11 to resist displacement of the second tab 30 in a longitudinal direction 31 toward the secondary bone zone 12.

The at least one barb is shown in the form of multiple barbs 33 extending in two parallel rows 33a and 33b along laterally opposite edges 34a and 34b of tab 30. The barbs have sharp tips 35 that are typically turned downwardly, as seen in FIG. 6, to frictionally engage, and penetrate the top surface 11a of the bone zone 11. Additional or alternate barbs on tab 30 are shown at 36, projecting downwardly from medial extent 37 of the tab, to engage surface 11a.

Tab 20 is attachable to the top surface 12a of bone zone 12, as by means of a fastener 23, that is driven downwardly through an opening 24 in tab 20. Opening 24 is an example of one anchor element for use in anchoring the first tab to the secondary bone zone.

Also provided is a retainer operatively connected with at least one of said tabs and projecting for retention to at least one of the bone zones at a retention level spaced from levels defined by the tabs. In the example, the retainer comprises a third tab 40 spaced from the first and second tabs 20 and 30, the tab 40 extending generally parallel to the second tab 30, and being integral with the first tab 20. Note that an upright leg or strut 41 is integral with and connected to ends of the horizontal tabs 20 and 40, and extends adjacent the edge 11c of the bone zone 11. The third tab 40 has a multiplicity of barbs oriented to engage the primary bone zone to resist displacement of the third tab in said direction toward the secondary bone zone. Such barbs extend in two parallel rows 42 and 43, which are laterally spaced, and have upwardly turned sharp tips 44. The latter engage the underside 11b of the bone zone 11 to resist rightward displacement of tab 40, toward bone zone 12. See also intermediate barbs 48 and 49.

Also provided is a projection associated with at least one of the tabs, and configured to engage the secondary bone zone at the edge thereof, and in spaced relation to said tabs. See for example the projection 50 on arm 51 integral with tab 30 at turn locus 52, the arm turned or extending downwardly to project through an opening 53' in first tab 20 overlying the gap 13. Arm 51 acts as a spring arm, for urging projection 50 toward edge 12a of bone zone 12. The projection 50 extends intermediate two parallel sections 51a and 51b of arm 51, as is seen in FIG. 8 showing a blank that forms 30 and 50. The projection has a sharp, tapering terminal 53 to enable penetration of diploe 16 at edge 12a, for anchoring arm 51 and tab 30 in position, as shown. The projection extend at angle α relative to a plane defined by tab 30.

The clip 10 accordingly is configured to have two associated components, the first component including tab 20, extension 41 and tab 40, defining a generally Z-shape. The second component includes tab 30, arm 51 and projection 50 also forming a generally Z-shape. Further, the two components are configured to interfit at the hinge location 52 where arm 51 extends downward through opening 53. Barbs on the two components are adapted to engage one of the bone zones to resist displacement of the two components relatively toward the other bone zone, as shown. FIG. 7 shows the first component in blank formed condition, prior to bending at 70 and 71, into generally Z-shape.

Accommodation to bone zones having different width gaps 13 therebetween is achieved by use of the spring arm 51 carrying projection 50.

I claim:

1. A clip to interconnect primary and secondary bone zones forming a gap therebetween, comprising
   a) first and second interfitting clip components, the first component having a first tab to engage a surface of the secondary bone zone the first component having generally Z-shaped configuration, and the second component having a second tab, an arm, and a projection forming a generally Z-shaped configuration, and wherein the second tab and projection extend in directions away from the arm,
   b) said first and second tabs adapted to engage surfaces defined by said first and second bone zones, and said projection adapted to engage an edge defined by the second bone zone,
   c) and wherein one of the Z-shaped components extends through and at opposite sides of an opening defined by the other Z-shaped component whereby the interfitting Z-shaped components define a hinge interfit at said opening and substantially at the level of said first tab.

2. The combination of claim 1, wherein
   e) said second tab has a multiplicity of barbs oriented to engage the primary bone to resist displacement of the second tab in a longitudinal direction toward the secondary bone zone,
   f) and the first component includes a third tab extending generally parallel to the second tab, and integral with said first tab,
   g) said third tab having a multiplicity of barbs oriented to engage the primary bone zone to resist displacement of the third tab in said direction toward the secondary bone zone,
   h) said multiplicity of barbs extending in two parallel generally longitudinal rows, at edges of each of the second and third tabs.

3. The combination of claim 2 wherein the third tab extends generally parallel to the second tab, and is integral with said first tab.

4. The combination of claim 2 wherein said second tab multiplicity of barbs extend in at least one row, in said direction.

5. The combination of claim 2 wherein said third tab multiplicity of barbs extend in two parallel generally longitudinal rows.

6. The combination of claim 5 wherein said barbs have sharp tips offset from a plane defined by the third tab.

7. The combination of claim 1 wherein said multiplicity of barbs on both the second and third tabs have sharp tips offset from planes defined by the respective second and third tabs.

8. The combination of claim 1 wherein said second tab has a multiplicity of barbs oriented to engage the primary bone zone to resist displacement of the second tab in said direction toward the secondary bone zone.

9. The combination of claim 8 wherein said multiplicity of barbs extend in at least one row, in said direction.

10. The combination of claim 8 wherein said multiplicity of barbs extend in two parallel generally longitudinal rows.

11. The combination of claim 10 wherein said barbs have sharp tips offset from a plane defined by the second tab.

12. The combination of claim 2 including an anchor element on the first tab for use in anchoring the first tab to the secondary bone zone.

13. The combination of claim 12 wherein anchor element comprises an opening through the tab.

14. The combination of claim 1 wherein the projection has a sharp terminal to enable penetration of diploe.

15. The combination of claim 14 wherein the projection extends at an acute angle relative to a plane defined by said one tab.

16. The combination of claim 1 including said primary and secondary bone zones having surfaces proximate which said primary and secondary tabs extend.

* * * * *